United States Patent
Sanchez Alonso (12)

(10) Patent No.: US 11,065,289 B1
(45) Date of Patent: Jul. 20, 2021

(54) SUBSTANCE AND METHOD FOR THE TREATMENT OF POXVIRUS

(71) Applicant: Elena Sanchez Alonso, Opa Locka, FL (US)

(72) Inventor: Elena Sanchez Alonso, Opa Locka, FL (US)

(*) Notice: Subject to any disclaimer, the term of this patent is extended or adjusted under 35 U.S.C. 154(b) by 0 days.

(21) Appl. No.: 17/129,246

(22) Filed: Dec. 21, 2020

(51) Int. Cl.
| | |
|---|---|
| *A61K 36/00* | (2006.01) |
| *A61K 36/22* | (2006.01) |
| *A61K 47/44* | (2017.01) |
| *A61K 9/00* | (2006.01) |

(52) U.S. Cl.
CPC ............ *A61K 36/22* (2013.01); *A61K 9/0014* (2013.01); *A61K 47/44* (2013.01); *A61K 2236/13* (2013.01); *A61K 2236/31* (2013.01); *A61K 2236/35* (2013.01); *A61K 2236/37* (2013.01); *A61K 2236/53* (2013.01)

(58) Field of Classification Search
None
See application file for complete search history.

(56) References Cited

U.S. PATENT DOCUMENTS

| | | |
|---|---|---|
| 9,694,068 B2 | 7/2017 | Golovkin |
| 10,220,066 B2 | 3/2019 | Angle |

FOREIGN PATENT DOCUMENTS

| | | | |
|---|---|---|---|
| CN | 108991488 A | * | 12/2018 |

* cited by examiner

*Primary Examiner* — Qiuwen Mi
(74) *Attorney, Agent, or Firm* — Sanchelima & Associates, P.A.; Christian Sanchelima; Alexander Rodriguez

(57) ABSTRACT

A substance for poxvirus molluscum infection treatment that includes a mixture of *Anacardium occidentale* seeds and sunflower oil is disclosed. The mixture is obtained by the washing, drying, and grinding of at least seven *Anacardium occidentale* seeds. The grinded seeds are then mixed in with at least one cup of sunflower oil. The mixture is then heated under a low temperature for a duration of at least ten minutes until the seeds are in a liquid or semi-liquid state. The temperature is then raised when the mixture begins to change color. The temperature is then lowered once the mixture ceases to produce smoke. The mixture is then strained and poured into sterile bottles which are wrapped in aluminum foil. When applied to a user, the mixture is then placed on a patch which is then placed on an infected area of a user's body.

12 Claims, 3 Drawing Sheets

SUBSTANCE AND METHOD FOR THE TREATMENT OF POXVIRUS

BACKGROUND OF THE INVENTION

1. Field of the Invention

The present invention relates to a substance and method for the treatment for poxvirus and, more particularly, to a substance and method for the treatment of poxvirus molluscum infections and skin symptoms of the human papilloma virus using a mixture of *Anacardium occidentale* seeds and sunflower oil.

2. Description of the Related Art

Several designs for a substance and method for the treatment of poxvirus have been designed in the past. None of them, however, include a substance for poxvirus molluscum infection treatment that includes a mixture of *Anacardium occidentale* seeds and sunflower oil. The mixture is obtained by the washing, drying, and grinding of at least seven *Anacardium occidentale* seeds. The grinded seeds are then mixed in with at least one cup of sunflower oil. The mixture is then heated under a low temperature for a duration of at least ten minutes until the seeds are in a liquid or semi-liquid state to form a substance. The temperature is then raised when the substance begins to change color. The temperature is then lowered once the substance ceases to produce smoke. The substance is then strained and poured into sterile bottles which are wrapped in aluminum foil. When applied to a user, the substance is then placed on a patch which is then placed on an infected area of a user's body. The substance can be applied to a user's body several times in one day to achieve desired results.

Applicant believes that a related reference corresponds to U.S. Pat. No. 10,220,066 issued for a treatment of virus-based diseases of the skin. The treatment includes topically administering an aqueous substance of plant oil extract from a dandelion to a patient's skin that is suffering from a virus-based disease. Applicant believes that another related reference corresponds to U.S. Pat. No. 9,694,068 issued for compositions and methods for procuring plant-derived compositions to aid the treatment of poxvirus molluscum infections. The plants are engineered to produce antigenic proteins. However, the cited references differ from the present invention because they fail to provide a substance and method derived from a mixture of *Anacardium occidentale* seeds and sunflower oil. The substance is then topically applied to the human skin for the treatment of poxvirus molluscum infections and other bacteria and skin infections resultant from human papilloma virus. The substance produced is oily in nature that allows the substance to be easily applied to the human skin.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a substance and method for the treatment of poxvirus molluscum infections which is safely topically administered to a patient's body through a patch placed on their skin.

It is another object of this invention to provide a substance and method for the treatment of poxvirus molluscum infections which aids in the treatment of poxvirus by reducing the symptoms manifested on a patient's skin, and prevents symptoms from recurring.

It is still another object of the present invention to provide a substance and method for the treatment of poxvirus molluscum infections which utilizes *Anacardium occidentale* seeds to create a substance for the treatment of poxvirus.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
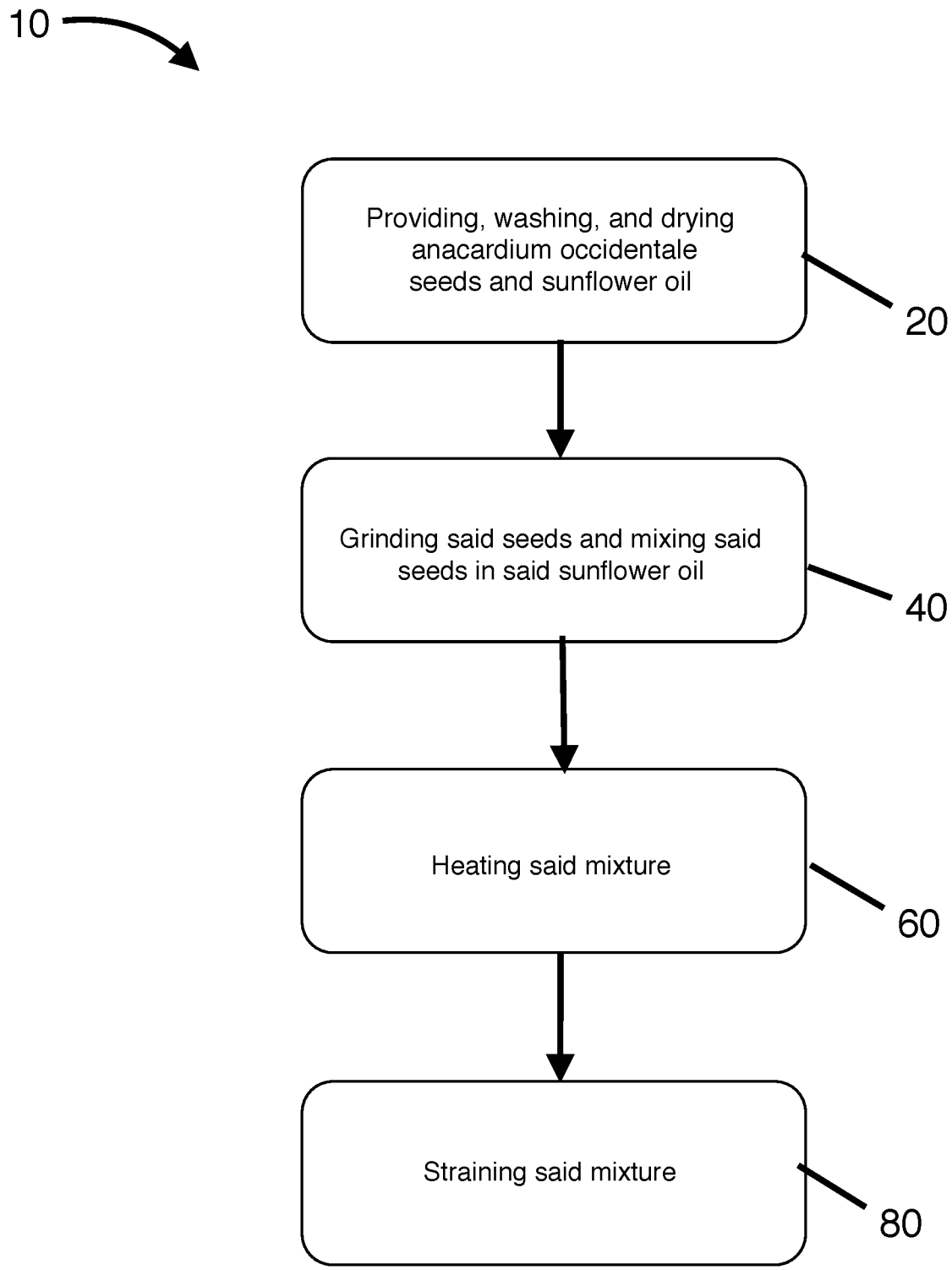
FIG. 1 represents a flow chart of process 10 in accordance with an embodiment of the present invention.
Figure 2:
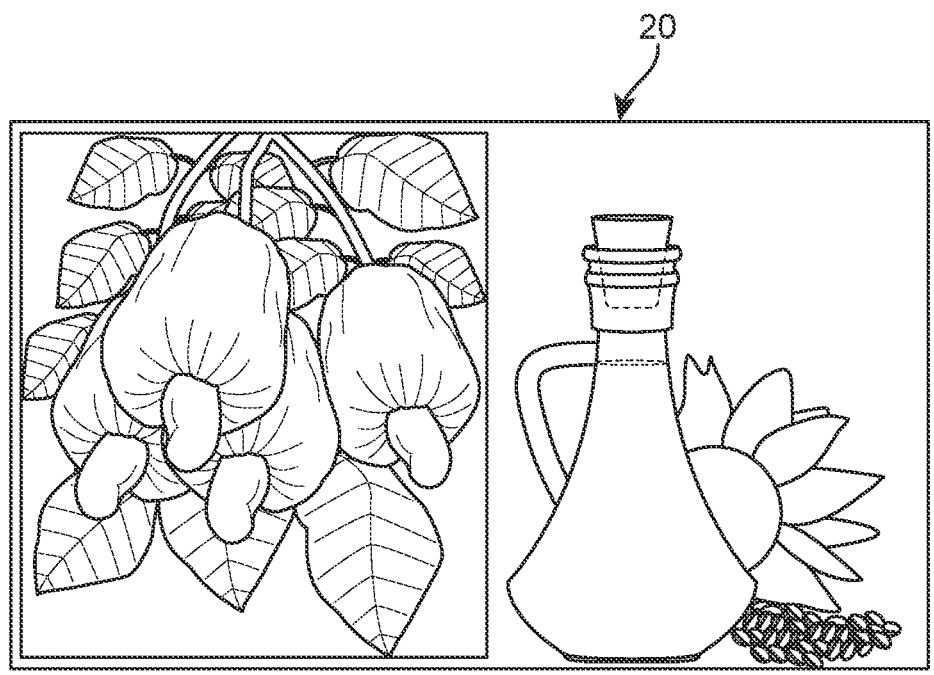
FIG. 2 shows an isometric view of first step 20 in accordance to an embodiment of the present invention.
Figure 3:
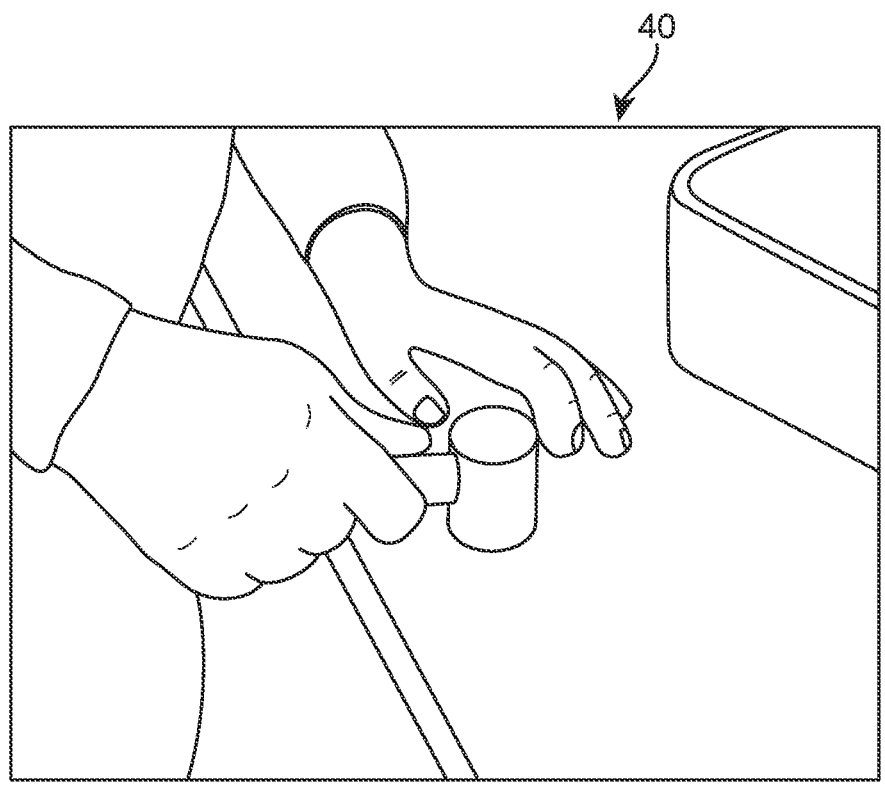
FIG. 3 illustrates an isometric view of second step 40 in accordance to an embodiment of the present invention.
Figure 4:
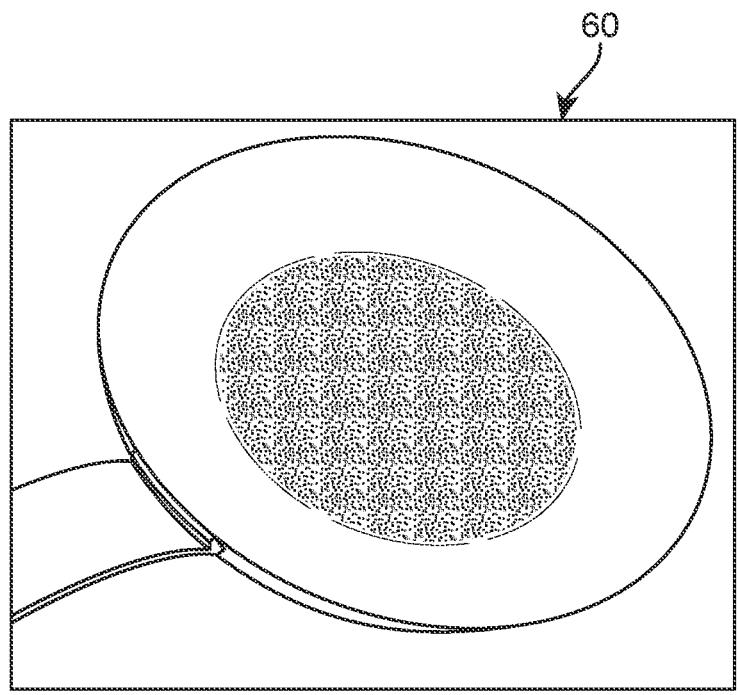
FIG. 4 is a representation of an isometric view of third step 60 in accordance to and embodiment of the present invention.
Figure 5:
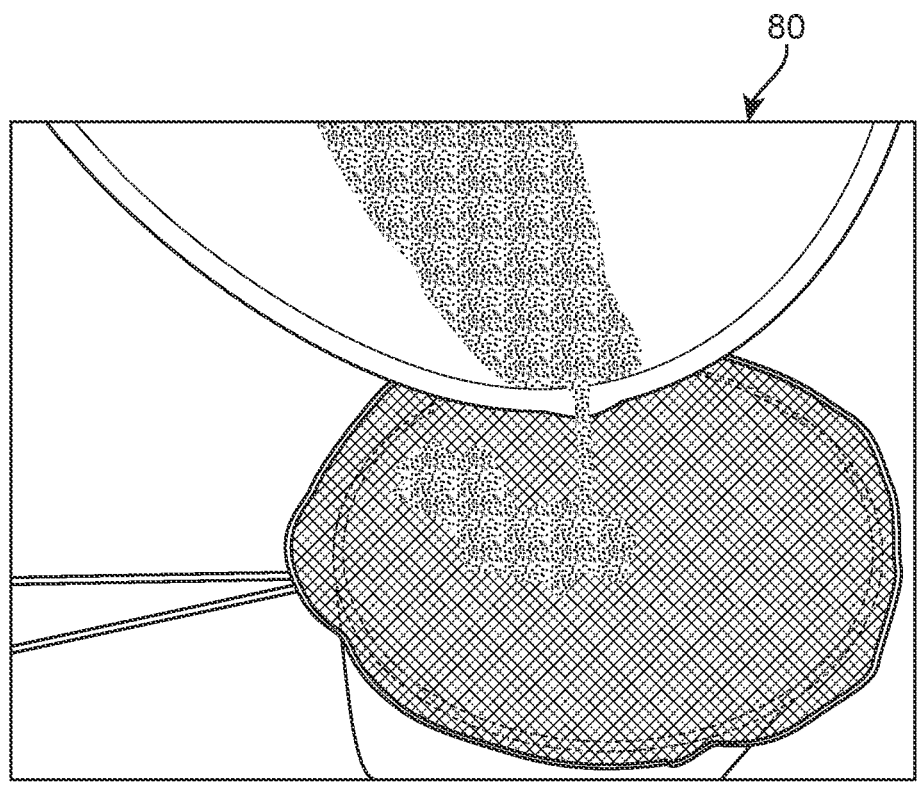
FIG. 5 shows an isometric view of fourth step 80 in accordance to an embodiment of the present invention.

Referring now to the drawings, where the present invention is generally referred to with numeral 10, it can be observed a process 10 for making a substance 100 for the treatment of poxvirus molluscum infections which basically includes a first step 20, a second step 40, a third step 60, and a fourth step 80.

First step 20 includes providing, washing and drying at least seven *Anacardium occidentale* seeds. The substance 100 will be include the extract from the pericarp and endocarp of the *Anacardium occidentale* seed. This seed contains various compounds and acids which targets the skin and positively affects the skin. The *Anacardium occidentale* seed includes anacardic acid which protects the user's skin. The seed also contains catechol which softens the targeted area of the skin. Furthermore, the seed contains resorcinol which helps with scarring in the skin and allows the substance to enter the resulting substance from the process in penetrating skin cells. Additionally, the seed contains hydroquinone and cardanol which aids in the pigmentation of the skin. In this first step the *Anacardium occidentale* seeds are gathered while they still have their green color. The seeds continue changing colors while drying. Afterwards, the *Anacardium occidentale* seeds are grounded up when they have a grey color.

The *Anacardium occidentale* seeds include phenol groups which are a class of chemical compounds consisting of one or more hydroxyl groups bounded directory to an aromatic hydrocarbon group. The phenol groups include Phenol OH and Phenols=C6 with chromatic rings C6—Cx³C₆ side chain carbon ridges containing catechol, resorcinol, and hydroquinone lipids. These lipids contain corrective properties which correct the dryness of human skin to retain water. Furthermore, the properties include moisturizing, protecting, softening, and reducing scarring and pain when applied to the human skin. This property allows the substance of the present invention to be effective in the treatment of poxvirus molluscum infections. The *Anacardium occidentale* seeds are grounded up when they have a grey color. Depending on the color and the stage of the seed will affect the amount of nutritional properties that are provided when implemented in the process. The grey seeds have been found to by richer in protein and in fat then their green counterpart. It should be understood that *Anacardium occidentale* seeds are capable of mutating and acquiring different shapes and sizes depending on how the seeds are bred. Other embodiments may feature other varieties of different *Anacardium occidentale* seeds with varying shapes, sizes and characteristics.

In first step 20, The *Anacardium occidentale* seeds are also washed and dried and placed in a grinding bowl. The seeds may also be placed in any other suitable environment for grinding the *Anacardium occidentale* seeds into a grainy texture. The seeds are grinded down to a grainy texture of particles measuring about less than 10 millimeters in diameter before proceeding into the next step.

Second step 40 includes grinding the seeds and mixing the grinded *Anacardium occidentale* seeds into at least one cup of sunflower oil as a vehicle to form a mixture. The sunflower oil is used to remove toxins found in the seeds. In the present embodiment, the seeds are grinded until they have a coarse and grainy texture as described above. It is important that the seeds have this texture when grinded as it will help the mixture form when it is eventually heated in third step 60. In the present embodiment, *Anacardium occidentale* seeds may be ground up by a hammer or similar means until the desired texture is achieved. Other embodiments may include using additional machinery to grind the seeds to their desired texture before mixing. However, one of the benefits of the present invention is that the desired texture may be achieved without the use of additionally machinery. The coarse texture allows for the beneficial elements of the *Anacardium occidentale* seeds to be more easily extracted.

In second step 40, sunflower oil is chosen specifically for its concentration of linoleic acid which plays a role in providing moisture to the skin without weighing down the skin. The linoleic acid further helps to fend off UV rays and air pollutants. Sunflower oil contains a concentration of about 68% linoleic acid which is the preferred concentration of linoleic acid needed for the process. Other types of oils which contain a concentration higher than 65% linoleic acid may be used. These oils may include but are not limited to safflower oil (78% concentration of linoleic acid), grape seed oil (73% concentration of linoleic acid), and evening primerose oil (74% of linoleic acid).

Third step 60 includes heating the mixture to form an oily substance. In one embodiment the process is heated with a temperature equal to or greater than 50 degrees Celsius. Additionally, the mixture is heated for a duration of at least 30 minutes. This will provide the necessary conditions to allow the nutrients of the *Anacardium occidentale* seeds to mix with the sunflower oil. In one embodiment, the *Anacardium occidentale* seeds are heated in the mixture until they are in a liquid or semi-liquid state forming an oily substance. There may be some solid particles remaining from the seeds. This state will indicate that a majority of the desired nutrients have been absorbed into the sunflower oil. Harmful components that include alcohol evaporate away before the majority or all of the beneficial components. Additionally, the substance is heated until the color of the seeds has changed. That is to say that the seeds have lost their original color further indicating that the nutrients of the seeds have been absorbed into the substance. In all cases notwithstanding the above, the heating temperature of the substance is lowered once the substance ceases to produce smoke in the heating process. The heating of the ancardic acid releases monophenol, cardanol, and resorcinol which acts as an antioxidant, anti-tumor, anti-viral, and anti-bacteria agent. The substance must then be cooled until it can be safely handled.

Fourth step 80 includes straining the substance that has been modified through the heating step of third step 60. The substance may be strained using any traditional strainer including straining bowls and straining cloths. The strained substance separates the mixture into two parts. The *Anacardium occidentale* seeds that were grinded and heated are then removed leaving behind the oily substance of the oil containing the beneficial nutrients of the *Anacardium occidentale* seeds. The seeds can be discarded and are not used any further in the process to produce the substance 100. The remaining part of the mixture is an oily substance which is substance 100 that is then used for the treatment of poxvirus molluscum infections. The resultant substance obtained from this process has a chemical formula of $CH_3$—$CH_2$—COOH and includes n-6 and n-3 series of polyunsaturated fatty acids. In one embodiment, the substance is strained and then stored into sterile bottles for storage. The sterile bottles aid the substance in maintaining the nutrients that were provided by the *Anacardium occidentale* seeds. Furthermore, the bottles may also be wrapped in aluminum foil to further aid the bottles in being maintained at a proper temperature and prevent the degradation of the substance contained therein. This step 80 can be repeated to obtain a resulting oily substance that includes less particles.

Substance 100 may then be topically applied to a human in need of relief and being affected by symptoms of poxvirus molluscum infections. The oily substance is topically applied to the skin of the human in need of relief of symptoms. In one embodiment the area of the skin is further provided with a patch to secure the topically applied substance in place and allow the substance to take effect and relieve the symptoms of the human in need. The substance contains various lipids which are beneficial to the human skin and aid in the treatment of poxvirus molluscum infections by inflammation and redness on the human skin. The substance also proves effective by reducing pain and inflammation caused by the human papilloma virus and may further be used to treat the skin for other inflammation relief. When obtained through process 10, substance 100 includes a chemical formula of $CH_3$—$CH_2$—COOH. Substance 100 contains various lipids that aid in the reduction of poxvirus symptoms. These lipids include catechol (specifically urushiol), resorcinol, and hydroquinone lipids, and belong to the n-6 and n-3 series of polyunsaturated fatty acids. When applied to the human skin, substance 100 proves effective in the treatment of poxvirus molluscum infections.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A process for creating a substance for the treatment of poxvirus molluscum infection, comprising:
   a) collecting *Anacardium occidentale* seeds;
   b) grinding said *Anacardium occidentale* seeds and mixing said *Anacardium occidentale* seeds into a predetermined amount of sunflower oil to form a mixture;
   c) heating said mixture and then lowering the heating temperature of said mixture once the mixture ceases to produce smoke thereby forming a substance; and
   d) straining said substance to remove seed particles.

2. The process for creating a substance for the treatment of poxvirus molluscum infection of claim 1 further including washing and drying said *Anacardium occidentale* seeds before grinding said *Anacardium occidentale* seeds.

3. The process for creating a substance for the treatment of poxvirus molluscum infection of claim 1 further including heating said mixture at a temperature greater than or equal to 50 degrees Celsius for at least 30 minutes.

4. The process for creating a substance for the treatment of poxvirus molluscum infection of claim 3 further including heating said mixture until said *Anacardium occidentale* seeds are in a liquid substance state containing said seed particles.

5. The process for creating a substance for the treatment of poxvirus molluscum infection of claim 1 further including straining said substance into sterile bottles.

6. The process for creating a substance for the treatment of poxvirus molluscum infection of claim 5 further including wrapping said sterile bottles in aluminum foil.

7. The process for creating a substance for the treatment of poxvirus molluscum infection of claim 1 wherein said substance includes a chemical composition of $CH_3-CH_2-COOH$.

8. The process for creating a substance for the treatment of poxvirus molluscum infection of claim 1 wherein said *Anacardium occidentale* seeds are provided when they have a grey color.

9. The process for creating a substance for the treatment of poxvirus molluscum infection of claim 1 wherein said *Anacardium occidentale* seeds are grinded to particles measuring less than 10 millimeters.

10. The process for creating a substance for the treatment of poxvirus molluscum infection of claim 1 further including repeating said straining of said substance to further remove said seed particles.

11. The process for creating a substance for the treatment of poxvirus molluscum infection of claim 1 wherein said predetermined amount of sunflower oil is 1 cup.

12. The process for creating a substance for the treatment of poxvirus molluscum infection of claim 1 wherein seven *Anacardium occidentale* seeds are provided.

* * * * *